(12) United States Patent
Sgroi

(10) Patent No.: US 10,603,042 B2
(45) Date of Patent: Mar. 31, 2020

(54) FLEXIBLE CIRCULAR STAPLER

(71) Applicant: Covidien LP, Mansfield, MA (US)

(72) Inventor: Anthony Sgroi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 425 days.

(21) Appl. No.: 15/421,687

(22) Filed: Feb. 1, 2017

(65) Prior Publication Data

US 2017/0224346 A1 Aug. 10, 2017

Related U.S. Application Data

(60) Provisional application No. 62/293,473, filed on Feb. 10, 2016.

(51) Int. Cl.
| | |
|---|---|
| *A61B 17/068* | (2006.01) |
| *A61B 17/115* | (2006.01) |
| *A61B 17/29* | (2006.01) |
| *A61B 17/00* | (2006.01) |
| *A61B 17/072* | (2006.01) |

(52) U.S. Cl.
CPC ...... *A61B 17/1155* (2013.01); *A61B 17/0682* (2013.01); *A61B 2017/0046* (2013.01); *A61B 2017/00398* (2013.01); *A61B 2017/00477* (2013.01); *A61B 2017/00862* (2013.01); *A61B 2017/07221* (2013.01); *A61B 2017/07257* (2013.01); *A61B 2017/07271* (2013.01); *A61B 2017/07285* (2013.01); *A61B 2017/2905* (2013.01)

(58) Field of Classification Search
CPC ........ A61B 17/1155; A61B 2017/1132; A61B 17/32053; A61B 18/1487; A61B 2017/00398; A61B 2017/0046; A61B 2017/00477; A61B 2017/00862; A61B 17/0682; A61B 2017/07221; A61B 2017/07257; A61B 2017/07271; A61B 2017/07285; A61B 2017/2905
USPC .......................................... 227/180.1, 179.1
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated May 3, 2017, issued in EP Appln. No. 17155482.

*Primary Examiner* — Robert F Long
*Assistant Examiner* — Patrick B Fry
(74) *Attorney, Agent, or Firm* — Carter DeLuca & Farrell LLP

(57) ABSTRACT

A circular stapler including a cartridge assembly and an anvil assembly is provided. The cartridge assembly includes a rotatable drive shaft and the anvil assembly includes first and second pull cables. When the anvil assembly engages the cartridge assembly, retraction of the first pull cable effects clamping of tissue between the anvil assembly and the cartridge assembly, and retraction of the second pull cable effects stapling and cutting of the clamped tissue.

20 Claims, 6 Drawing Sheets

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A * | 10/1990 | Hervas ................. A61B 17/115 227/179.1 |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A * | 12/1993 | Grant ................. A61B 17/115 227/179.1 |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,465,894 A * | 11/1995 | Clark ................. A61B 17/072 227/175.1 |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A * | 1/1999 | Toledano ............. A61B 17/115 227/176.1 |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |

(56) References Cited

U.S. PATENT DOCUMENTS

| | | | |
|---|---|---|---|
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 * | 1/2002 | Toledano ............ A61B 17/115 |
| | | | 227/175.1 |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 * | 9/2002 | Whitman ......... A61B 17/07207 |
| | | | 227/176.1 |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,565 B1 * | 2/2003 | Whitman ......... A61B 17/07207 |
| | | | 600/146 |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 * | 9/2005 | Gresham ............ A61B 17/115 |
| | | | 227/175.1 |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,625,385 B2 * | 12/2009 | Fortier ............ A61B 17/00234 |
| | | | 606/140 |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |

(56) References Cited

U.S. PATENT DOCUMENTS

| | | |
|---|---|---|
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 * | 9/2011 | Whitman ............ A61B 17/115 227/155 |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,351,734 B2 * | 5/2016 | Prior ............ A61B 17/115 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |

(56) References Cited

U.S. PATENT DOCUMENTS

| | | |
|---|---|---|
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| FR | 2689749 A1 | 10/1993 |
| GB | 1185292 A | 3/1970 |
| GB | 2016991 A | 9/1979 |
| GB | 2070499 A | 9/1981 |
| JP | 2004147969 A | 5/2004 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2008/107918 A1 | 9/2008 |

* cited by examiner

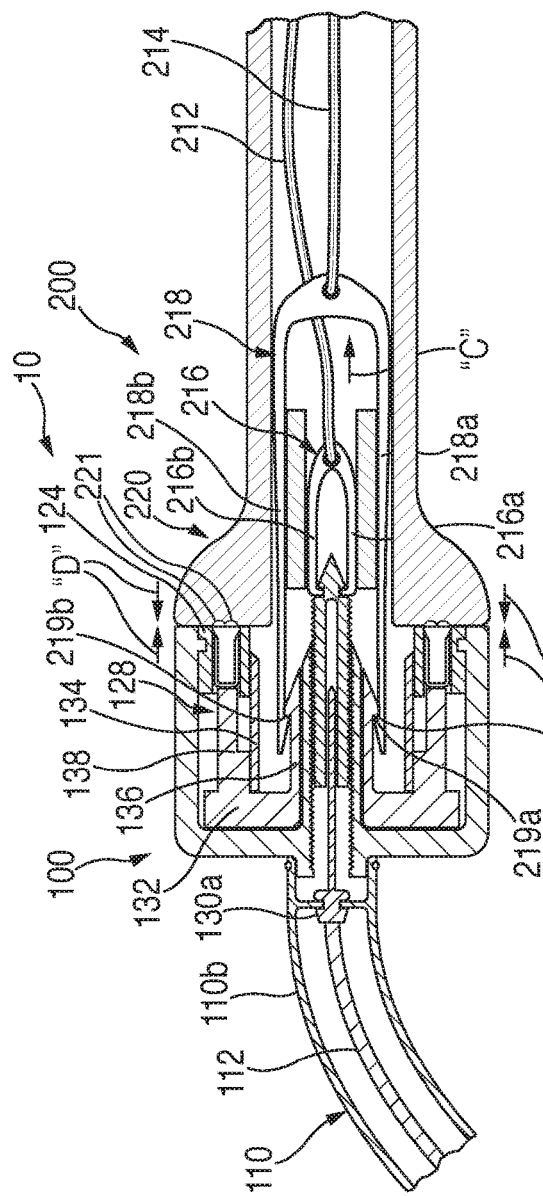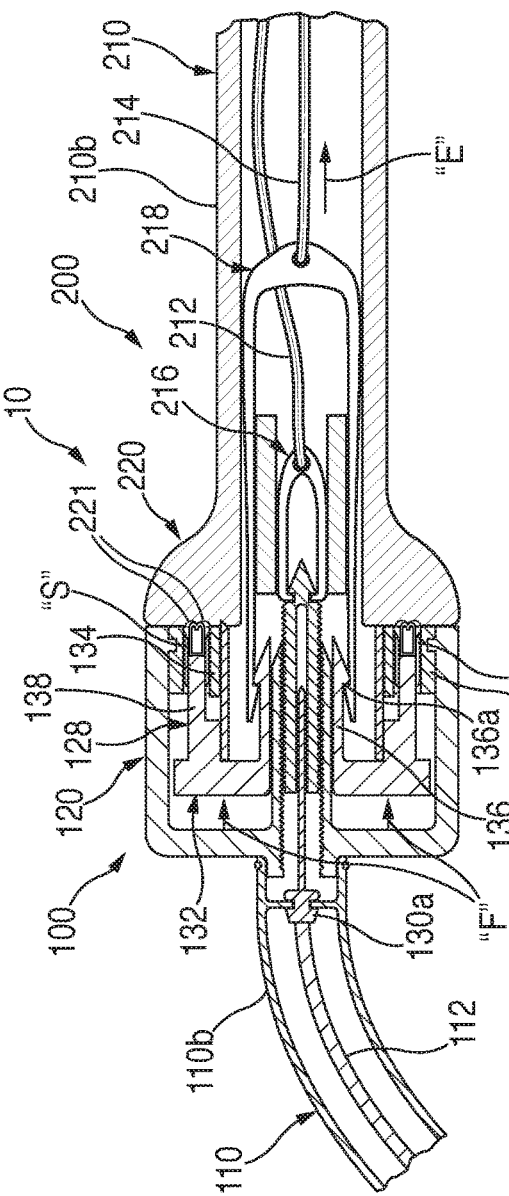

FLEXIBLE CIRCULAR STAPLER

CROSS-REFERENCE TO RELATED APPLICATIONS

This application claims the benefit of and priority to U.S. Provisional Patent Application No. 62/293,473 filed Feb. 10, 2016, the entire disclosure of which is incorporated by reference herein

BACKGROUND

Technical Field

The present disclosure relates to surgical stapler devices. More particularly, the present disclosure relates to flexible circular staplers.

Background of Related Art

Circular staplers are used to perform end to end anastomosis. A typical circular stapler includes an anvil assembly releasably securable relative to a cartridge assembly disposed on a distal end of an elongate shaft. Operation of the circular stapler requires actuation of a handle assembly disposed on a proximal end of the elongate shaft to first retract the anvil assembly relative to the cartridge assembly to clamp tissue, and then to advance or push one or more actuation assemblies to staple and cut tissue. The flexibility of the elongate shaft of the circular stapler is limited because of the rigidity of the drive shafts required for actuation of the pusher assemblies.

Accordingly, it would be beneficial to have a circular stapler in which operation of one or more actuation assemblies is achieved with a pulling action.

SUMMARY

A circular stapler having a cartridge assembly and an anvil assembly is provided. The cartridge assembly includes a loading unit having a staple cartridge, a plurality of staples received within the staple cartridge, and a pusher assembly movable relative to the staple cartridge. The anvil assembly includes an anvil member, and a first pull cable extending through the anvil member and engagable with the pusher assembly. Retraction of the first pull cable causes the pusher assembly to move relative to the staple cartridge to eject the plurality of staples from the staple cartridge.

In embodiments, the cartridge assembly includes a trocar member and the anvil assembly includes a second pull cable. The second pull cable may be engageable with the trocar member to approximate the loading unit relative to the anvil member. The cartridge assembly may further include a drive shaft operably connected to the trocar member. The trocar member may be threaded. Rotation of the drive shaft may cause longitudinal movement of the trocar member within the loading unit.

The circular stapler may further include a first actuation assembly secured to the cartridge assembly for effecting rotation of the drive shaft. The first actuation assembly may include a powered handle assembly. The circular stapler may further include a second actuation assembly secured to the anvil assembly for effecting retraction of the first and second pull cables. The second actuation assembly may include a manually powered handle assembly. The manually powered handle assembly may include a first handle member secured to the first pull cable and a second handle member secured to the second pull cable.

In some embodiments, the pusher assembly includes a circular knife for cutting tissue. The anvil member may define staple forming pockets corresponding with the plurality of staples supported with staple cartridge. The cartridge assembly may include an elongate body. The loading unit may be supported on a distal end of the elongate body. The anvil assembly may include a support tube. The anvil member may be supported on a distal end of the support tube.

An anastomosis stapling system is also provided. The system includes a cartridge assembly, an anvil assembly, a first actuation assembly operably connectable to the cartridge assembly, and a second actuation assembly operably connectable to the anvil assembly. The cartridge assembly includes a trocar member movable from a retracted position to an extended position. The anvil assembly includes at least one cable. The first actuation assembly moves the trocar member between the retracted and extended positions. The second actuation assembly selectively retracts the at least one cable. The first actuation assembly may include a powered handle assembly. The second actuation assembly may include a manually powered handle assembly.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 6 is a side cross-sectional view of the cartridge assembly shown in FIG. 3 and the anvil assembly shown in FIG. 4 operably secured together; and FIG. 7 is a side cross-sectional view of the cartridge assembly and the anvil assembly shown in FIG. 6, during a stapling procedure.

DETAILED DESCRIPTION

Figure 1:
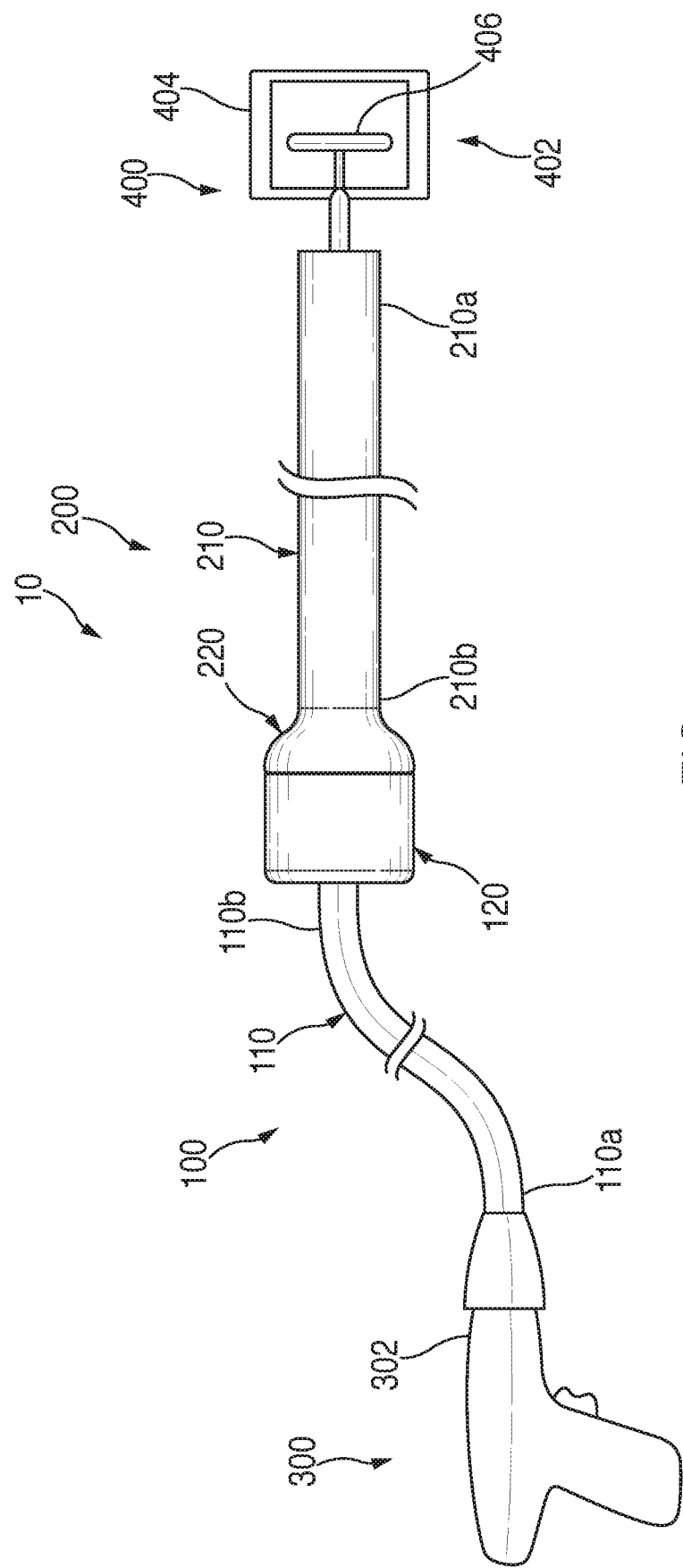
FIG. 1 is a side perspective view of a circular stapling apparatus according to an embodiment of the present disclosure.

Embodiments of the disclosure are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

With reference to FIG. 1, a circular stapling apparatus according to an embodiment of the present disclosure is shown generally as circular stapler 10. The circular stapler 10 includes a cartridge assembly 100 releasably securable to an anvil assembly 200. As will be described in further detail below, the cartridge assembly 100 is actuated through operation of the anvil assembly 200.

The cartridge assembly 100 includes an elongate body 110, a drive shaft 112 (FIG. 2) extending through the elongate body 110, and a loading unit 120 secured to a distal end 110b of the elongate body 110. The drive shaft 112 may be a flexible, torsionally stiff member capable of flexing or bending and capable of transmitting rotational forces. A first actuation assembly 300 is secured to a proximal end 110a of the elongate body 110 of the cartridge assembly 120. The first actuation assembly 300 may be releasably secured to the elongate body 110 to permit reuse of the first actuation assembly 300. As shown, the first actuation assembly 300 includes a powered handle assembly 302. As will become apparent from the following disclosure, the first actuation assembly 300 may include any mechanism suitable for rotating the drive shaft 112 (FIG. 2) extending through the elongate body 110 of the cartridge assembly 100. For a detailed description of an exemplary powered handle assembly, please refer to commonly owned U.S. Pat. Appl. Publ. No. 2012/0253329 ("the '329 application"), the content of which is incorporated by reference herein in its entirety.

The anvil assembly 200 includes a support tube 210, and an anvil member 220 secured to a distal end 210b of the support tube 210. The anvil member 220 may be integrally formed with the support tube 210, e.g, monolithic, or otherwise secured thereto.

A second actuation assembly 400 is secured to a proximal end 210a of the support tube 210. The second actuation assembly 400 may be releasably secured to the support tube 210 to permit reuse of the second actuation assembly 400. As shown, the second actuation assembly 400 includes a manual handle assembly 402 having a first handle member 404 and a second handle member 406. As will become apparent from the following disclosure, the second actuation assembly 400 may include any mechanism suitable for pulling first and second actuation cables 214, 216 (FIG. 3) extending through the support tube 210 of the anvil assembly 200.

Figure 2:
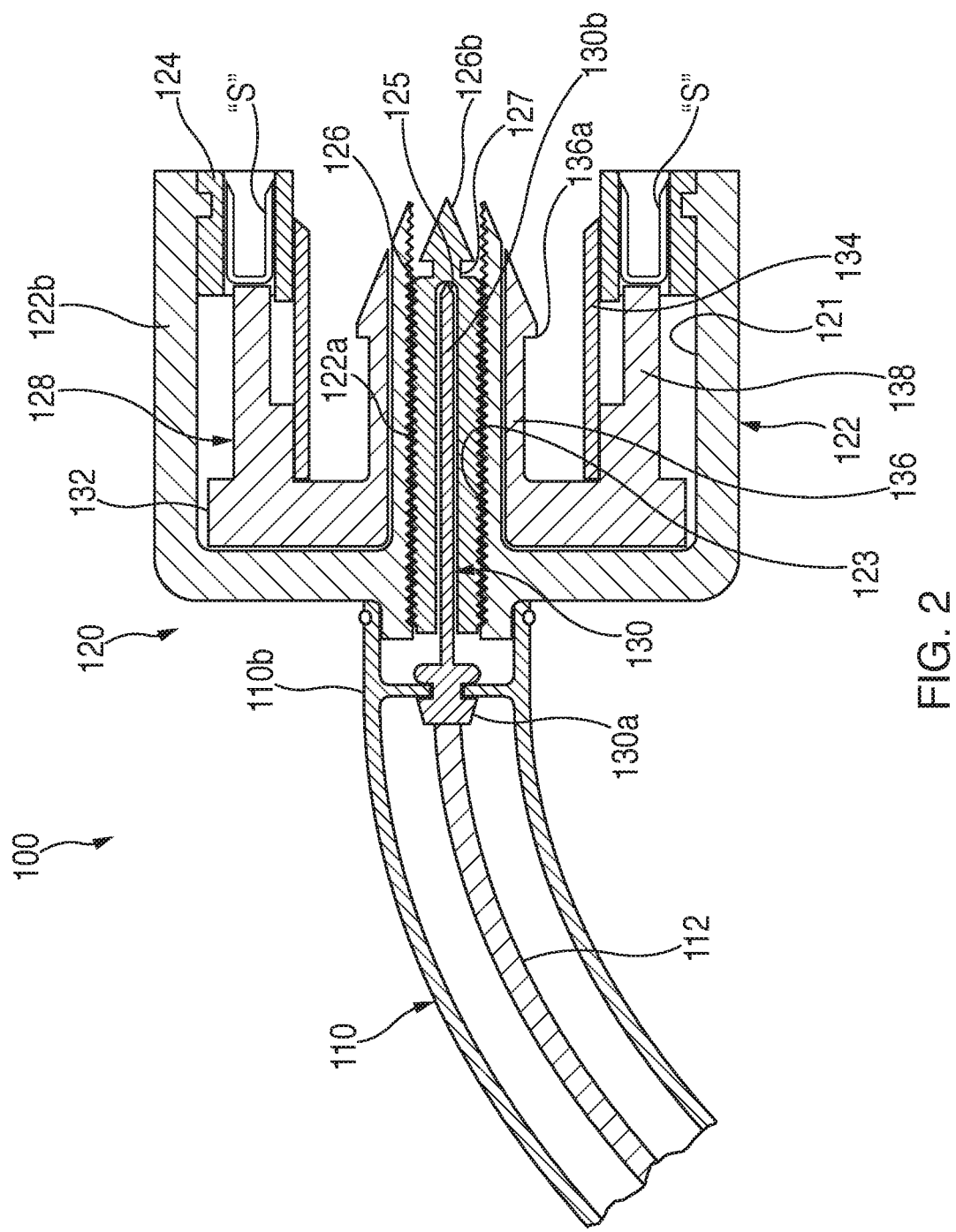
FIG. 2 is a side cross-sectional view of a cartridge assembly of the circular stapling apparatus shown in FIG. 1.

With reference now to FIG. 2, the loading unit 120 of the cartridge assembly 100 includes a shell member 122, a staple cartridge 124 supported on the shell member 122, a threaded trocar member 126 extendible from the shell member 122, and a pusher assembly 128 operably supported with the shell member 122. The shell member 122 includes an inner wall 122a and an outer wall 122b, and defines an annular recess 121 between the inner and outer walls 122a, 122b for receiving the pusher assembly 128. The inner wall 122a defines a threaded longitudinal bore 123 for receiving the threaded trocar member 126.

The threaded trocar member 126 of the loading unit 120 is rotatably received within the threaded longitudinal bore 123 of the inner wall 122a of the shell member 122. Rotation of the threaded trocar member 126 causes longitudinal movement, i.e., extension or retraction, of the threaded trocar member 126 relative to the shell member 122. The threaded trocar member 126 includes a pointed distal end 126b and defines an annular groove 127. The threaded trocar member 126 further defines a longitudinal bore 125 for receiving a drive member 130 secured to the drive shaft 112. In particular, a proximal portion 130a of the drive member 130 is rotatably received within the elongate body 110 of the cartridge assembly 100 and is connected to a distal end of the drive shaft 112. A distal portion 130b of the drive member 130 includes a cross-section corresponding to a cross-section of the longitudinal bore 125 of the threaded trocar member 126. In this manner, the drive member 130 is keyed to the threaded trocar member 126, such that rotation of the drive member 130 causes corresponding rotation of the threaded trocar member 126.

With continued reference to FIG. 2, the staple cartridge 124 of the cartridge assembly 100 supports one or more circular arrays of staples "S" on a distal end of the shell member 122. The staples "S" may be supported within the staple cartridge 124 in any arrangement. The staple cartridge 124 may be configured to supports staples "S" of different sizes and configurations. If is further envisioned that the staple cartridge 124 may be modified to support a first part (not shown) of a two part fastener (not shown).

The pusher assembly 128 of the cartridge assembly 100 includes a pusher member 132 receivable within the annular recess 123 of the shell member 122 and about the inner wall 122a of the shell member 122, and a circular knife 134 secured to the pusher member 132. The pusher assembly 128 is movable between a first, retracted position (FIG. 2) and a second, extended position (FIG. 7) to effect the stapling and cutting of tissue (not shown). While shown and described as occurring simultaneously, it is envisioned that the staple and cut functions may occur independently.

The pusher member 132 of the pusher assembly 128 includes a flange portion 136 configured for operable engagement with a second connector clip 218 of the anvil assembly 200 (FIG. 3), and a pusher portion 138 configured for operable engagement with, and deformation of, the staples "S" in the staple cartridge 124. In particular, the flange portion 136 of the pusher member 132 includes a ridge 136a configured for engagement with protrusions 219a, 219b of the second connector clip 218. A free end of the flange portion 136 of the pusher member 132 may include a frustoconical shape, as shown, to facilitate securing of the cartridge assembly 100 with the anvil assembly 200.

Figure 3:
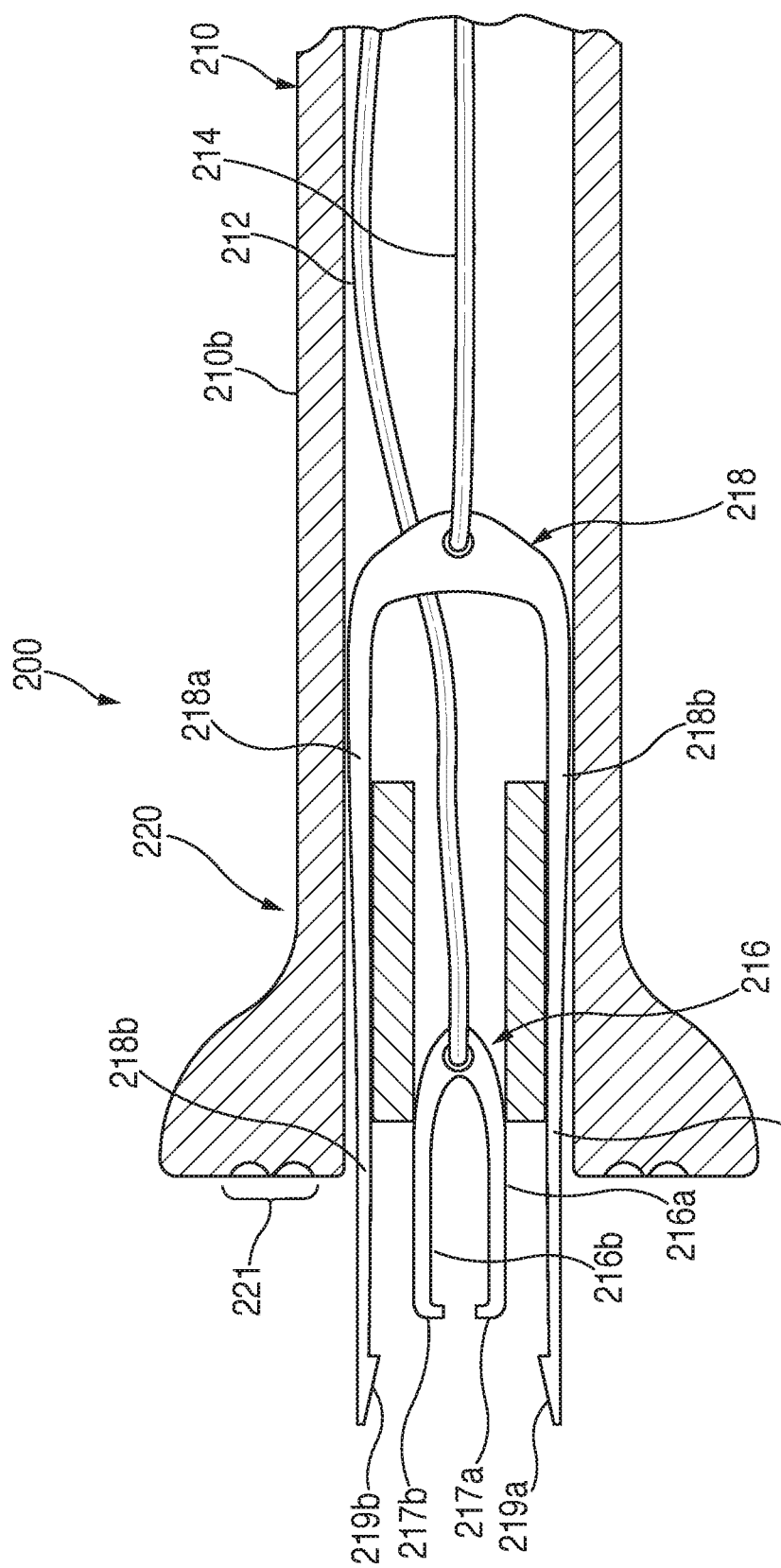
FIG. 3 is a side cross-sectional view of an anvil assembly of the circular stapling apparatus shown in FIG. 1.

Turning now to FIG. 3, the anvil assembly 200 includes the support tube 210, first and second pull cables 212, 214 extending through the support tube 210, first and second connector clips 216, 218 secured to the distal end of the respective first and second pull cables 212, 214, and the anvil member 220 disposed on a distal end 210b of the support tube 210. The anvil member 220 may be integrally formed with the support tube 210, i.e., monolithic, or secured thereto using adhesive, welding, fasteners, crimping or in any other suitable manner. The anvil member 220 defines a plurality of staple forming pockets 221 corresponding to the staples "S" supported within the staple cartridge 124 of the loading unit 120 of the cartridge assembly 100. As noted above, the staples "S" may be supported within the staple cartridge 124 in any arrangement. Accordingly, the staple forming pockets 221 may also include any arrangement corresponding to the arrangement of staples "S" of the staple cartridge 124.

As will be described in further detail below, the first connector clip 216 operably engages the threaded trocar member 126 of the loading unit 120 of the cartridge assembly 100, and retraction of the first pull cable 212 effects approximation of the loading unit 120 and the anvil member 220, i.e., clamping of tissue (not shown). The second connector clip 218 operably engages the pusher member 128 of the loading unit 120 of the cartridge assembly 100 and retraction of the second pull cable 214 effects longitudinal movement of the pusher member 128, i.e., stapling and cutting of tissue (not shown).

With continued reference to FIG. 3, the first and second connector clips 216, 218 are moveably supported within the anvil member 220 of the anvil assembly 200. The first connector clip 216 includes first and second arms 216a, 216b configured to engage the threaded trocar member 128 of the loading unit 120 of the cartridge assembly 100. More particularly, the first and second arms 216a, 216b of the first connector clip 216 each include an inward projection 217a, 217b, respectively, configured to be received within the annular groove 127 of the threaded trocar member 126 of the cartridge assembly 100.

Similarly, the second connector clip 218 includes first and second arms 218a, 218b configured to engage the pusher member 132 of the pusher assembly 128 of the loading unit 120 of the cartridge assembly 100. More particularly, the first and second arms 218a, 218b of the second connector clip 218 each include an inward projection 219a, 219b, respectively, configured to engage the flange portion 136 of the pusher member 132 of the cartridge assembly 100. Although the first and second connector clips 216, 218 are shown as including pairs of arms 216a, 216b, 218a, 218b, it is envisioned that the first and second connector clips 216, 218 may include any number of arms. In embodiments, the first and second connector clips 216, 218 are tubular and the inward projections (not shown) extend entirely about an inner surface of the tubular walls.

Figure 4A:
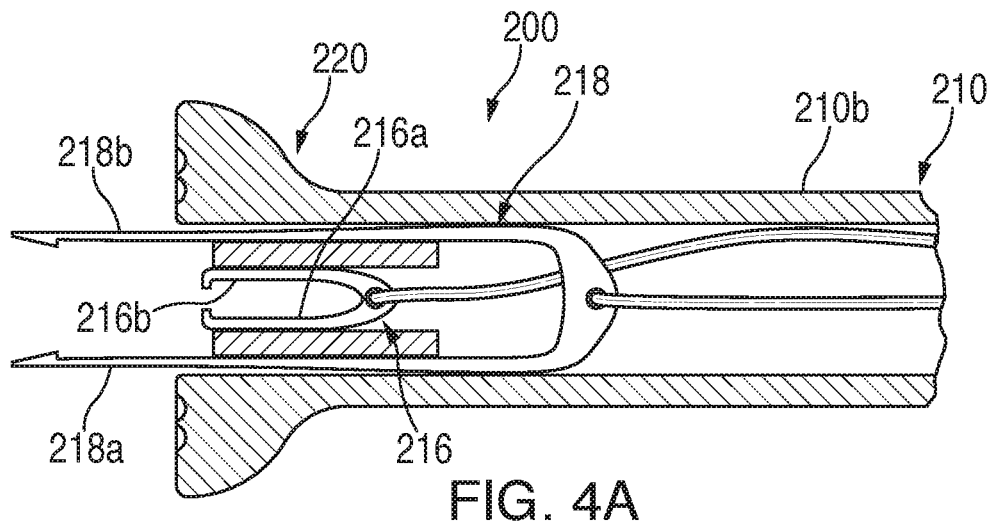
FIG. 4A is a side cross-sectional views of the anvil assembly shown in FIG. 3, with a first clip member in an extended position and a second clip member in a retracted position.
Figure 4B:
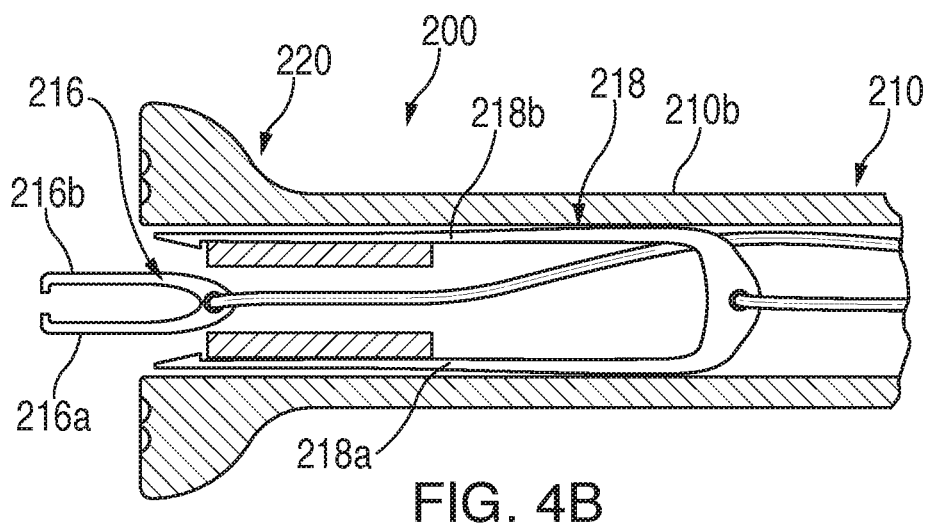
FIG. 4B is a side cross-sectional views of the anvil assembly shown in FIG. 4A, with the first clip member in a retracted position and the second clip member in an extended position.
Figure 4C:
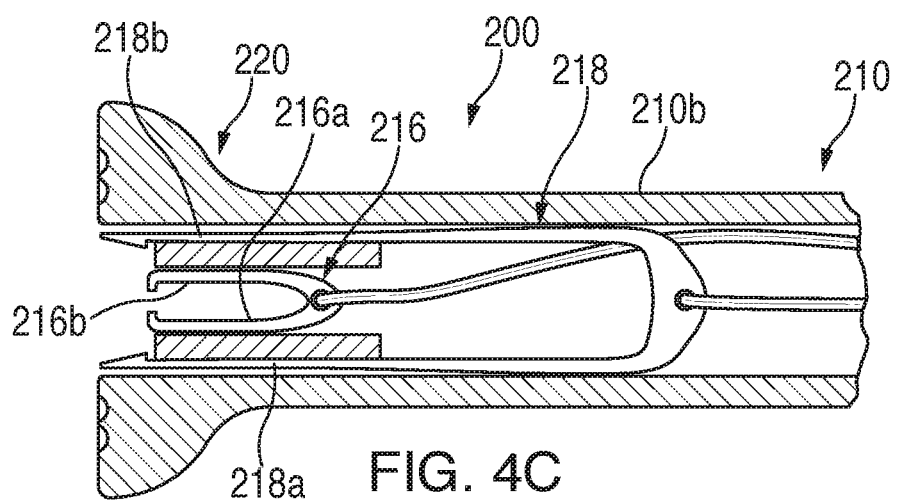
FIG. 4C is a side cross-sectional views of the anvil assembly shown in FIG. 4A, with the first clip member in its extended position and the second clip member in its extended position.

The first and second connector clips 216, 218 are disposed within the anvil member 220 of the anvil assembly 200 to facilitate operable engagement of the anvil member 220 with the loading unit 120 of the cartridge assembly 100. Depending on preference of the clinician, the condition of the tissue to be stapled, and/or other circumstances arising during the stapling procedure using the stapling apparatus 10, in embodiments, the first and second connector clips 216, 218 of the anvil assembly 200 may both extend from the anvil member 220 (FIG. 3); the second connector clip 218 may extend from the anvil member 220 while the first connector clip is retained within the anvil member 220 (FIG. 4A), the first connector clip 216 may extend from anvil member 220 while the second connector clip 218 is retainer within anvil member 220 (FIG. 4B); or the first and second connector clips 216, 218 may both be retained within the anvil member 220. (FIG. 4C).

Although the first and second pull cables 212, 214 are shown and described as only operating to retract the respective first and second connector clips 216, 218 relative to the anvil member 220 of the anvil assembly 200, it is envisioned that the first and/or second pull cables 212, 214 may be rigid enough to permits pushing of the respective first and second connector clips 216, 218 such that either or both of the respective first and second connector clips 216, 218 may be advanced relative to the anvil member 220 of the anvil assembly 200.

Figure 5:
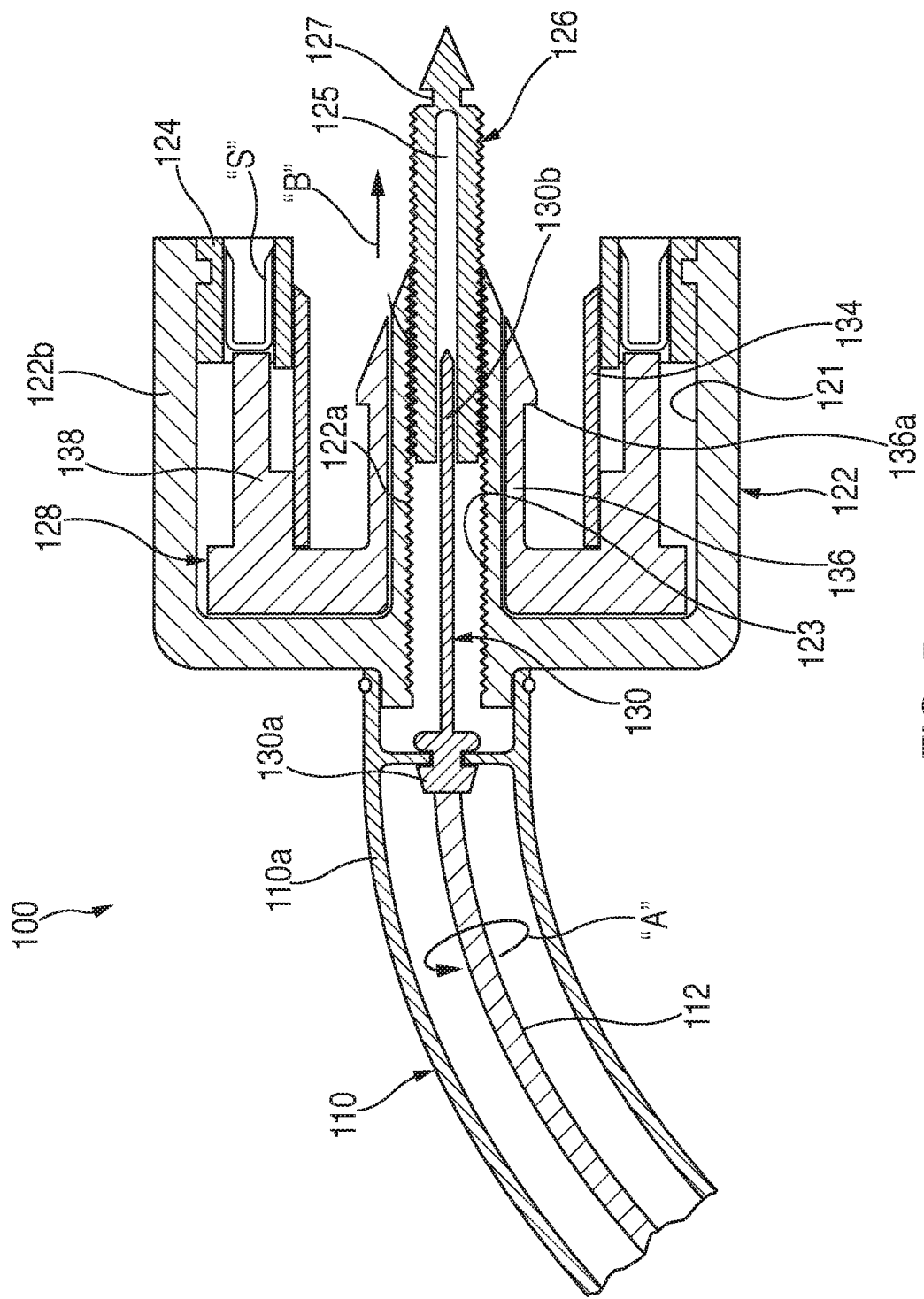
FIG. 5 is a side cross-sectional view of the cartridge assembly shown in FIG. 2, with a trocar member in an extended position.

The operation of circular stapler 10 will now be described with reference to FIGS. 5-7. Referring initially to FIG. 5, the loading unit 120 of the cartridge assembly 100 is shown with the threaded trocar member 126 in its extended position. The threaded trocar member 126 is typically retained in its retracted position (FIG. 2) during introduction of the cartridge assembly 100 to a surgical site. The flexible nature of the drive shaft 112 permits trans-oral, or anal introduction of the loading unit 120 to the surgical site. The first actuation assembly 300 may be used to facilitate introduction of the loading unit 120 to the surgical site. Alternatively, or in addition, a removable introducter (not shown) may be received on a distal end of the loading unit 120 to facilitate introduction of the loading unit 120 to the surgical site.

Once received in a desired location, the drive shaft 112 is rotated in a first direction, as indicated by arrow "A" in FIG. 5, to cause rotation of the drive member 130 and corresponding rotation of the threaded trocar member 126 causes extension of the threaded trocar member 126, as indicated by arrow "B" in FIG. 5. As noted above, the drive shaft 112 may be manually rotated or rotated through the use of the powered handle assembly 302 (FIG. 1). The pointed distal end 126b of the threaded trocar member 126 may be used to pierce tissue (not shown) and retain the tissue about the loading unit 120 in preparation for a stapling procedure.

As noted above, depending on the preference of the clinician, and/or the parameters of the stapling procedure, the first and second connector clips 216, 218 of the anvil assembly 200 may be disposed within the anvil member 220 in a variety of configuration. Either of the first and second arms 216a, 216b, 218a, 218b of the first and second connector clips 216, 218, respectively, may be used to pierce tissue (not shown) and/or retain the tissue about the anvil member 220 in preparation for a stapling procedure.

Turning to FIG. 6, once the sections of tissues to be stapled (not shown) are received over respective loading unit 120 of the cartridge assembly 100 and the anvil member 220 of the anvil assembly 200, the loading unit 120 and the anvil member 220 are positioned relative to each other such that the first connector clip 216 engages the threaded trocar member 126 and the second connector clip 218 engages the flange portion 136 of the pusher member 132 of the pusher assembly 128. Regardless of the initial configuration of first and second connector clips 216, 218 of the anvil assembly 200, receipt of the inward projections 217a, 217b of respective first and second arms 216a, 216b of the first connector clip 216 within the annular groove 127 of the threaded trocar member 126 secures the first connector clip 216 with the threaded trocar member 126.

Retraction of the first pull cable 212, as indicated by arrow "C" in FIG. 6, moves the first connector clip 216 and the attached threaded trocar member 126 of the cartridge assembly 100 relative to the anvil member 220 of the anvil assembly 200 to approximate the loading unit 120 of the cartridge assembly 100 relative to the anvil member 220. In embodiments, and as shown, the first pull cable 212 is pulled using the second handle member 406 (FIG. 1) of the manual handle assembly 402 (FIG. 1) of the second actuation assembly 400. Alternatively, the first pull cable 212 may be pulled using a powered handle assembly (not shown), similar to the powered handle assembly 300, or in any other suitable manner. In addition, or alternatively, it is envisioned that the drive shaft 112 of the cartridge assembly 100 may be rotated in a second direction to cause the retraction of the threaded trocar member 126 relative to the anvil member 220 of the anvil assembly 200, thereby approximating the anvil member 220 relative to the loading unit 120 of the cartridge assembly 100.

If the second connector clip 218 of the anvil assembly 200 is has not already engaged the pusher member 132 of the pusher assembly 128 of the cartridge assembly 100 prior to approximating the loading unit 120 and the anvil member 220, when the first pull cable 212 of the anvil assembly 200 is pulled to approximate the loading unit 120 and the anvil assembly 220, the second connector clip 218 is moved into engagement with the pusher member 132 of the loading unit 120. More particularly, as the loading unit 120 moves relative to the anvil member 220, the inward projections 219a, 219b of the respective first and second arms 218a, 218b of the second connector clip 218 engage the ridge 136a formed on the flange portion 136 of the pusher member 132. Engagement of either or both of the first and second connector clips 216, 218 with the respective threaded trocar member 126 and pusher member 132 may produce an audible and/or tactile indication to the clinician that the first and second connector clips 216, 218 are secured to the respective threaded trocar member 126 and pusher member 132.

With reference now to FIG. 7, once the loading unit 120 of the cartridge assembly 100 and the anvil member 220 of the anvil assembly 200 are approximated, the second pull cable 214 is pulled, as indicated by arrow "E" in FIG. 7, to cause the retraction of the second connector clip 218. As the second connector clip 218 is retracted, the engagement of the second connector clip 218 with the pusher member 132 of the pusher assembly 128 of the loading unit 120 causes the pusher member 132 to moved relative to the anvil member 220 of the anvil assembly 200, as indicated by arrow "F" in FIG. 7. As the pusher member 132 is moved towards the anvil member 220, the pusher portions 138 of the pusher member 132 engage the staples "S" to push the staples "S" from within the staple cartridge 124 into the staple forming pockets 221 of the anvil member 220 to cause the stapling of tissue received between the loading unit 120 and the anvil member 220.

Simultaneously with the stapling of tissue received between the loading unit 120 and the anvil member 220, the circular knife 124 that is secured to the pusher member 132 of the pusher assembly 128 is advanced through tissue to cut tissue. The pusher assembly 128 may be configured such that the circular knife 124 cuts tissue (not shown) as the tissue is being stapled, or subsequent to the tissue stapling. This may occur through simultaneously through a single actuation of the stapling device 10 (FIG. 1), or separately through independent actuations of the stapling device 10 (FIG. 1).

Following the stapling procedure, the anvil member 220 of the anvil assembly 200 is moved away from the loading unit 120 of the cartridge assembly 100 by releasing the tension on the first and second pull cables 212, 214 to permit the respective first connector clip 216 and the attached threaded trocar member 126 of the loading unit 120 to withdraw from within the anvil member 220 and the second connector clip 218 and the attached pusher assembly 128 to return to an initial position. It is envisioned that the loading unit 120 of the cartridge assembly 100 may include one or more biasing members, i.e., compression springs, for returning the pusher assembly 128 to its retracted position within the shell member 122 of the loading unit 120.

Once the stapled and cut tissue is removed from between the loading unit 120 and the anvil member 220, the circular stapler 10 is removed from within the patient. It is envisioned that, in one embodiment, the elongate body 110 of the cartridge assembly 100 is separated from the first actuation assembly 400 and the cartridge assembly 100 is removed through the same opening, i.e., laparoscopic incision, as the anvil assembly 200. Alternatively, the anvil assembly 200 may be separated from the second actuation assembly 400 and the anvil assembly 200 is removed through the same opening, i.e., mouth, as the cartridge assembly 100.

The increased flexibility of the elongate body 110 of the cartridge assembly 100 provided by having only a single flexible drive shaft 120 and the increased flexibility of the support tube 210 of the anvil assembly 200 provided by having first and second pull cables 212, 214 instead of drive shafts enables greater manipulability and adaptability of the circular stapler 10.

The cartridge assembly 100 and the anvil assembly 200 may be provided as an anastomosis stapling system, i.e., a kit, further including the first and second actuation assemblies 300, 400. It is envisioned that the anvil assembly 200 may be configured for multiple uses during the same procedure and/or may be sterilized and used in subsequent procedures. Accordingly, the anastomosis stapling system may include more than one cartridge assembly 100 for use with the anvil assembly 200. It is further envisioned that the anastomosis stapling system may include replacement loading units 120 for permitting reuse of the cartridge assembly 100.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A circular stapler comprising:
a cartridge assembly including a loading unit having a trocar member, a staple cartridge, a plurality of staples received within the staple cartridge, and a pusher assembly movable relative to the staple cartridge; and
an anvil assembly releasably securable to the cartridge assembly, the anvil assembly including an anvil member, and first and second pull cables extending through the anvil member, the first pull cable engageable with the trocar member and the second pull cable engageable with the pusher assembly, wherein retraction of the first pull cable causes the cartridge and anvil assemblies to approximate and retraction of the second pull cable causes the pusher assembly to move relative to the staple cartridge to eject the plurality of staples from the staple cartridge.

2. The circular stapler of claim 1, wherein the cartridge assembly further includes a drive shaft operably connected to the trocar member and the trocar member is threaded, wherein rotation of the drive shaft causes longitudinal movement of the trocar member within the loading unit.

3. The circular stapler of claim 2, further including a first actuation assembly secured to the cartridge assembly for effecting rotation of the drive shaft.

4. The circular stapler of claim 3, wherein the first actuation assembly includes a powered handle assembly.

5. The circular stapler of claim 3, further including a second actuation assembly secured to the anvil assembly for effecting retraction of the first and second pull cables.

6. The circular stapler of claim 5, wherein the second actuation assembly includes a manually powered handle assembly.

7. The circular stapler of claim 6, wherein the manually powered handle assembly includes a first handle member secured to the first pull cable and a second handle member secured to the second pull cable.

8. The circular stapler of claim 1, wherein the pusher assembly includes a circular knife for cutting tissue.

9. The circular stapler of claim 1, wherein the anvil member defines staple forming pockets corresponding with the plurality of staples supported with staple cartridge.

10. The circular stapler of claim 1, wherein the cartridge assembly includes an elongate body, and the loading unit is supported on a distal end of the elongate body.

11. The circular stapler of claim 1, wherein the anvil assembly includes a support tube, and the anvil member is supported on a distal end of the support tube.

12. The circular stapler of claim 11, wherein the support tube is flexible.

13. The circular stapler of claim 1, wherein the cartridge assembly is supported on a distal end of an elongate body.

14. The circular stapler of claim 13, wherein the elongate body is flexible.

15. The circular stapler of claim 1, wherein retraction of the second pull cable in a first direction causes movement of the pusher assembly in the first direction.

16. The circular stapler of claim 15, wherein retraction of the first pull cable in the first direction causes the cartridge and anvil assemblies to approximate.

17. An anastomosis stapling system comprising:
a cartridge assembly including a trocar member movable from a retracted position to an extended position;
an anvil assembly including at least one cable;
a first actuation assembly operably connectable to the cartridge assembly for moving the trocar member between the retracted and extended positions; and
a second actuation assembly operably connectable to the anvil assembly for selectively retracting the at least one cable, wherein the first actuation assembly is disposed on a first end of the anastomosis stapling system and the second actuation assembly is disposed on a second end of the anastomosis stapling system.

18. The anastomosis stapling system of claim 17, wherein the first actuation assembly includes a powered handle assembly.

19. The anastomosis stapling system of claim 17, wherein the second actuation assembly includes a manually powered handle assembly.

20. The anastomosis stapling system of claim 17, wherein the first end of the anastomosis stapling system is longitudinally spaced from the second end.

* * * * *